United States Patent [19]

Brown et al.

[11] Patent Number: 4,954,224
[45] Date of Patent: Sep. 4, 1990

[54] EXTRACTIVE DISTILLATION OF HYDROCARBON FEEDS EMPLOYING MIXED SOLVENT

[76] Inventors: Ronald E. Brown, 6419 Quail Ridge Rd.; Fu M. Lee, 645 Castle Dr., both of Bartlesville, Okla. 74006

[21] Appl. No.: 404,704

[22] Filed: Sep. 8, 1989

[51] Int. Cl.$^5$ .............................................. B01D 3/40
[52] U.S. Cl. ........................................ 203/51; 203/56; 203/58; 203/64; 203/65; 203/68; 585/865; 585/867
[58] Field of Search .................. 203/58, 64, 68, 51, 203/56, 65; 585/865, 867

[56] References Cited

U.S. PATENT DOCUMENTS

| | | | |
|---|---|---|---|
| 2,508,723 | 5/1950 | Mayland et al. | 585/866 |
| 2,679,472 | 5/1954 | Tooke | 203/60 |
| 2,695,322 | 11/1954 | Weedman | 585/839 |
| 2,736,755 | 2/1956 | Reuter et al. | 55/84 |
| 2,771,494 | 11/1956 | Weedman | 585/836 |
| 2,786,804 | 3/1957 | Nelson | 203/60 |
| 2,809,925 | 10/1957 | Nelson | 203/60 |
| 2,839,452 | 6/1958 | Nelson | 203/60 |
| 2,846,485 | 8/1958 | Mason et al. | 585/866 |
| 2,891,894 | 6/1959 | Cier et al. | 203/60 |
| 3,034,969 | 5/1962 | Makin, Jr. | 203/60 |
| 3,114,783 | 12/1963 | Butler et al. | 203/43 |
| 3,301,911 | 1/1967 | Boatright | 585/866 |
| 3,349,009 | 10/1967 | Ruehlen | 203/67 |
| 3,591,490 | 7/1971 | Müller et al. | 208/313 |
| 3,860,496 | 1/1975 | Ginnasi et al. | 203/28 |
| 4,031,148 | 6/1977 | Helgorsky | 570/238 |
| 4,053,369 | 10/1977 | Cines | 203/52 |
| 4,121,978 | 10/1978 | Becuwe | 203/58 |
| 4,278,505 | 6/1981 | Danulat et al. | 203/59 |
| 4,498,980 | 2/1985 | Forte | 208/321 |
| 4,514,262 | 4/1985 | Berg | 203/51 |
| 4,690,733 | 9/1987 | Forte et al. | 203/21 |

OTHER PUBLICATIONS

"Extractive Distillation Saves Energy", by Ian Sucksmith, Chemical Engineering, Jun. 29, 1987, pp. 91–95.
"Handbook of Separation Techniques for Chem. Engineers", by Philip Schweitzer, McGraw Hill Book Co., 1979, pp. 1–135 to 1–143.
"Perry's Chemical Engineers' Handbook", 6th Edition, McGraw Hill Book Co., 1984, p. 13-53 to 13-57.

Primary Examiner—Virginia Manoharan

[57] ABSTRACT

Cycloalkanes (preferably cyclopentane and/or cyclohexane) are separated from close-boiling alkanes by extractive distillation employing as solvent a mixture of (a) at least one N-mercaptoalkyl-2-pyrrolidone (preferably N-mercaptoethyl-2-pyrrolidone) and (b1) at least one N-alkyl-2-pyrrolidone (preferably N-methyl-2-pyrrolidone) and/or (b2) at least one saturated $C_5$–$C_9$ alcohol (preferably cyclohexanol).

27 Claims, 1 Drawing Sheet

EXTRACTIVE DISTILLATION OF HYDROCARBON FEEDS EMPLOYING MIXED SOLVENT

BACKGROUND OF THE INVENTION

In one aspect, this invention relates to the separation of saturated cycloaliphatic hydrocarbons (cycloalkanes, naphthenes) from close-boiling saturated aliphatic hydrocarbons (alkanes, paraffins) by extractive distillation. In another aspect, this invention relates to the use of mixtures of organic compounds as solvent (also referred to as extractant or entrainer) in the aforementioned extractive distillation. In a further aspect, this invention relates to novel mixtures of organic compounds.

Extractive distillation is a well known technique for separating mixtures of components having a relative volatility close to unity (i.e., having nearly equal volatility and having nearly the same boiling point). It is difficult to separate the components of such mixtures by conventional fractional distillation. In extractive distillation, a solvent is introduced into a distillation column above the entry point of the feed mixture which is to be separated. The solvent affects the volatility of the higher boiling feed component(s) sufficiently to facilitate the separation of the various feed components by distillation and exits with the bottoms fraction, as has been described in the article entitled "Extractive Distillation Saves Energy" by Ian Sucksmith, Chemical Engineering, June 28, 1982, pages 91–95, the disclosure of which is herein incorporated by reference. Other literature sources on extractive distillation techniques include the "Handbook of Separation Techniques for Chemical Engineers" by Philip A. Schweitzer, McGraw-Hill Book Company, 1979, pages 1-135 to 1-143; and Perry's Chemical Engineers Handbook, 6th Edition, McGraw-Hill Book Company, 1984, pages 13–53 to 13–57, the disclosures of which are herein incorporated by reference.

The separation of naphthenes (cycloparaffins), in particular cyclohexane, from close-boiling paraffins by extractive distillation is known and has been described in the patent literature, such as in U.S. Pat. Nos. 2,508,723; 2,771,494; 2,846,485; 2,891,894; 3,034,969 and 4,053,369, the disclosures of which are herein incorporated by reference. However, there is an ever present need to develop more selective solvents than those presently known in the extractive distillation of mixtures of close-boiling paraffins and naphthenes. In particular, it is highly desirable to develop improved extractive distillation processes for producing cyclohexane of high purity, which is a starting material for making nylon and other useful polymeric materials.

SUMMARY OF THE INVENTION

It is an object of this invention to provide a process for separating mixtures of close-boiling naphthenes (cycloalkanes) and paraffins (alkanes) by extractive distillation employing a mixture of organic compounds as solvent. It is another object of this invention to produce cyclohexane of high purity from a mixture comprising cyclohexane and close-boiling isoparaffins (i.e., isoparaffins having nearly the same volatility as cyclohexane) by extractive distillation employing a mixture of organic compounds as solvent. It is a further object of this invention to provide a novel mixture of organic compounds. Other objects and advantages will be apparent from the detailed description of the invention and the appended claims.

In accordance with this invention, in a process for separating at least one cycloalkane (naphthene) containing 5–10 carbon atoms per molecule from at least one close-boiling alkane (paraffin), i.e., one or a plurality of alkanes having nearly the same boiling point at atmospheric pressure conditions as said cycloalkane, by extractive distillation of a feed comprising (preferably consisting essentially of) said at least one cycloalkane and said at least one alkane, the improvement is the use of a solvent (also referred to as extractant or entrainer) comprising (preferably consisting essentially of) a mixture of (a) at least one N-mercaptoalkyl-2-pyrrolidone, wherein the mercaptoalkyl group contains 1–5 (preferably 1–3) carbon atoms per molecule, and (b1) at least one N-alkyl-2-pyrrolidone, wherein the alkyl group contains 1–3 carbon atoms.

In a preferred embodiment, the feed cycloalkane is cyclohexane. In another preferred embodiment, component (a) of the solvent is N-($\beta$-mercaptoethyl)-2-pyrrolidone. In a further preferred embodiment, component (b1) of the solvent is N-methyl-2-pyrrolidone.

Also in accordance with this invention, in a process for separating at least one cycloalkane containing 5–10 carbon atoms per molecule from at least one close-boiling alkane, by extractive distillation of a feed comprising (preferably consisting essentially of) said at least one cycloalkane and said at least one alkane, the improvement is the use of a solvent comprising (preferably consisting essentially of) a mixture of component (a), as defined above, and (b2) at least one saturated aliphatic alcohol (alkanol) and/or saturated cycloaliphatic alcohol (cycloalkanol) containing 5–9 carbon atoms and 1 OH group per molecule.

In a preferred embodiment, the feed cycloalkane is cyclopentane or cyclohexane or a mixture of both. In another preferred embodiment, component (a) of the solvent is N-($\beta$-mercaptoethyl)-2-pyrrolidone. In a further preferred embodiment, component (b2) of the solvent is cyclohexanol.

Further in accordance with this invention, compositions of matter are provided comprising a mixture of (preferably consisting essentially of) either components (a) and (b1), or components (a) and (b2); or components (a), (b1) and (b2), as defined above. In preferred embodiments, component (a) is N-($\beta$-mercaptoethyl)-2-pyrrolidone, component (b1) is N-(methyl)-2-pyrrolidone, and component (b2) is cyclohexanol. The above-described mixtures can be used as solvents (extractants) in the extractive distillation of hydrocarbon mixtures.

DETAILED DESCRIPTION OF THE INVENTION

Figure 1:
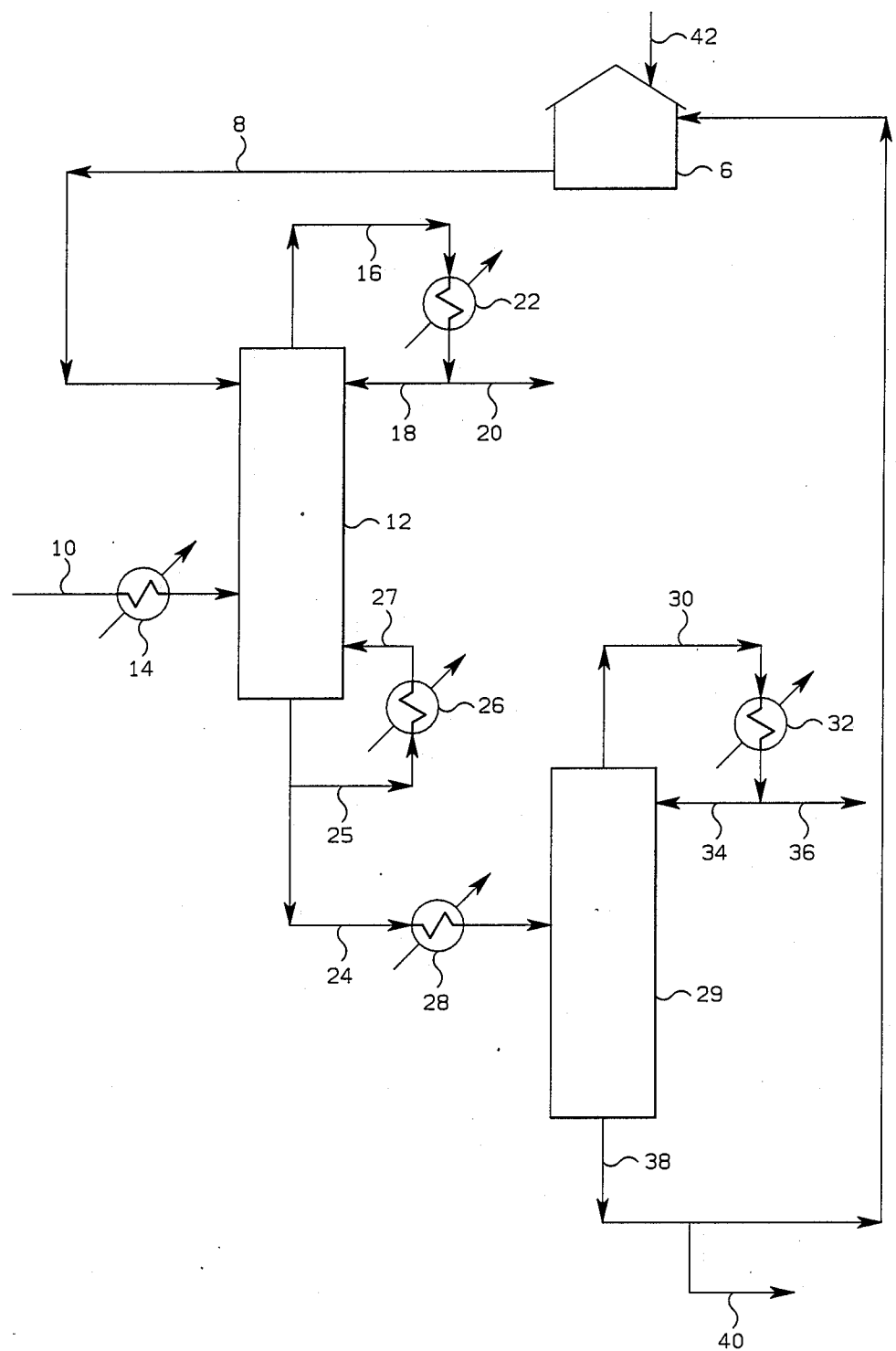
FIG. 1 illustrates the extractive distillation process of this invention.

In an extractive distillation process, an agent (called "solvent" or "extractant" or "entrainer") is added to a feed mixture of components to be separated so that the relative volatilities of the components of the mixture are changed such that a sufficient difference in volatility of the components results and effective separation by distillation becomes possible. The added solvent is usually chosen so as to exhibit high "selectivity" regarding the components to be separated. Selectivity is a term related to the change in volatilities of components in the mixture caused by the presence of the solvent. The larger the difference in relative volatility of the components in the mixture, the easier the separation of the components by fractional distillation becomes. Therefore, a solvent of high selectivity is a solvent which causes great differences between the relative volatilities of the components in a mixture, and will allow for the separation of components in a mixture with fewer distillation stages, lower amount of reflux and higher product purity.

Any hydrocarbon feed which contains at least one cycloalkane (naphthene) containing 5–10 carbon atoms per molecule and at least one close-boiling alkane (preferably containing 5–10 carbon atoms per molecule, more preferably branched alkane or isoparaffin) can be used in the process of this invention. Generally, the feed contains about 1–98 weight-% cycloalkane(s) and about 2–99 weight-% alkane(s), preferably about 10–95 weight-% cycloalkane(s) and about 5–90 weight-% alkane(s). Preferably, the feed is substantially free of aromatic hydrocarbons. Preferably, the boiling point (at atmospheric pressure conditions, i.e., at about 1 atm.) of the cycloalkane(s) and alkane(s) to be separated by extractive distillation is in the range of from about 80° to about 350° F., more preferably about 100°–300° F. Generally, the boiling points of the cycloalkane(s) and the alkane(s) differ by about 0.2°–10° F. (preferably about 0.5°–5° F.), at about 1 atm.

Non-limiting examples of cycloalkanes are cyclopentane, cyclohexane, methylcyclopentane, cycloheptane, 1,1-dimethylcyclopentane, 1,2-dimethylcyclopentane, 1,3-dimethylcyclopentane, ethylcyclopentane, methylcyclohexane, 1,1-dimethylcyclohexane, 1,2-dimethylcyclohexane, 1,3-dimethylcyclohexane, ethylcyclohexane, cyclooctane, and the like, and mixtures thereof. Presently preferred are cyclopentane and cyclohexane.

Non-limiting examples of alkanes are n-pentane, n-hexane, 2-methylpentane, 3-methylpentane, n-heptane, 2,2-dimethylpentane, 2,4-dimethylpentane, 3,3-dimethylpentane, 2,3-dimethylpentane, 2-methylhexane, 3-methylhexane, 2,2,3-trimethylbutane, n-octane, 2-methyloctane, n-nonane, and the like, and mixtures thereof.

The general structural formula of N-mercaptoalkyl-2-pyrrolidones, which are useful as component (a) of the solvent in the process of this invention, is

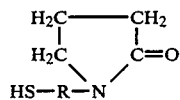

wherein R is a radical selected from the group consisting of —CH$_2$—, —CH$_2$—CH$_2$—, —CH$_2$—CH$_2$—CH$_2$—, —CH(CH$_3$)—CH$_2$—, —CH$_2$—CH(CH$_3$)—CH(CH$_3$)—, —C(CH$_3$)$_2$—CH(CH$_3$)—, —CH$_2$—CH$_2$—CH$_2$—CH$_2$—, —CH$_2$—CH$_2$—CH$_2$—CH$_2$—CH$_2$—, and the like, and mixtures thereof. The preferred radical R is —CH$_2$—CH$_2$—. Thus, the preferred solvent is N-($\beta$-mercaptoethyl)-2-pyrrolidone:

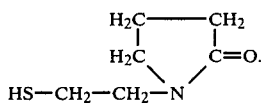

Examples of component (b1) of the solvent include N-methyl-2-pyrrolidone (presently preferred), N-ethyl-2-pyrrolidone and N-propyl-2-pyrrolidone.

The N-(mercaptoalkyl)-2-pyrrolidones can be prepared by UV-catalyzed addition of H$_2$S to the corresponding N-alkenyl-2-pyrrolidone. For instance, N-($\beta$-mercaptoethyl)-2-pyrrolidone is prepared by reaction of H$_2$S and N-vinyl-2-pyrrolidone, at room temperature (about 25° C.) and a molar ratio of H$_2$S to N-vinyl-2-pyrrolidone of about 5–6:1, while the reaction mixture is continuously exposed to UV radiation. Generally, the reaction is carried out with stirring and UV irradiation for about 4–6 hours. The formed product, N-($\beta$-mercaptoethyl)-2-pyrrolidone, (boiling point: 266° C. at 1 atm; 100° C. at 0.3 mm Hg) is separated from unreacted N-vinyl-2-pyrrolidone by fractional distillation.

Non-limiting examples of alcohols which are suitable as component (b2) of the solvent are cyclopentanol, 2-methylcyclopentanol, 3-methylcyclopentanol, cyclohexanol (preferred), 2-methylcyclohexanol, 3-methylcyclohexanol, 2,3-dimethylcyclohexanol, cycloheptanol, 2-methylcycloheptanol, 3-methylcycloheptanol, 4-methylcycloheptanol, 2,3-dimethylcycloheptanol, n-hexanol, 2-methyl-1-hexanol, 3-methyl-1-hexanol, 3-methyl-2-hexanol, n-heptanol, 2-methyl-1-heptanol, 3-methyl-1-heptanol, 3-methyl-2-heptanol, 2,3-dimethyl-1-heptanol, n-octanol, mixtures thereof, and the like.

Any suitable weight ratio of component (b1) or (b2) to component (a) in the solvent (also called extractant) of this invention can be employed in the extractive distillation process of this invention. Preferably, the weight ratio of component (a) to either component (b1) or component (b2) or the sum of components (b1)+(b2) (if applicable) is in the range of from about 0.1:1 to about 20:1, more preferably from about 0:5 to about 5:1.

Any suitable weight ratio of the solvent to the hydrocarbon containing feed mixture can be employed. Preferably, the solvent to feed weight ratio is in the range of from about 0.5:1 to about 50:1, more preferably from about 3:1 to about 20:1.

Any suitable reflux ratio (i.e., the weight ratio of the portion of condensed vapor which is returned to the distillation column to the portion of condensed vapor which is withdrawn as distillate) can be employed in the process of this invention. Generally the reflux ratio is in the range of from about 0.1:1 to about 100:1, preferably in the range of from about 0.5:1 to about 50:1, more preferably in the range of from about 1:1 to about 40:1.

Any suitable feed entry location can be selected. Generally the feed entry location is in the range of from about 2 to about 70 percent of the total height of the packed or trayed column, measured upward from the bottom of the column, preferably in the range of from about 5 to about 60 percent, more preferably in the range of from about 7 to about 70 percent.

Any suitable solvent entry location can be selected. Generally the solvent entry location is in the range of from about 50 to about 99 percent of the total height of the packed or trayed column (i.e., within the upper half of the column), preferably in the range of from about 70 to about 99 percent, more preferably in the range of from about 80 to about 99 percent.

Any suitable temperature in the reboiler vessel (containing primarily the higher boiling feed components and the solvent) can be employed. The temperature is generally in the range of from about 100° to about 400° F., preferably in the range of from about 150° to about 320° F. The extractive distillation column is generally heated (more near the bottom, and less near the top). Generally, the temperature at the top of the column where the vapor exits into the condenser is in the range of from about 100° to about 300° F., preferably in the range of from about 150° to about 250° F. Solvent and feed are generally preheated (generally to a temperature close to the column temperature of the corresponding entry point) before they are introduced into the packed column. Any suitable pressure can be employed during the extractive distillation. Generally the pressure is about 5 to about 100 psig, preferably about 8 to about 20 psig.

Generally, the overhead distillate (withdrawn from the top of the column) contains a smaller volume percentage of cycloalkanes (preferably cyclopentane and/or cyclohexane) than the feed and a larger volume percentage of alkanes (preferably isoalkanes) than the feed. Generally, the bottoms product (a portion of which can be reheated and recycled to the lower portion of the column) contains more cycloalkanes than the feed, and less alkanes (preferably isoalkanes) than the feed. Furthermore, the bottoms product contains essentially all of the added solvent, which can be separated from the other bottoms product components by distillation or other suitable separating means and then be recycled to the extractive distillation column.

Any suitable total column height, packed column height, column diameter and number of trays in the extraction distillation column can be employed. The exact dimensions and column designs depend on the scale of the operation, the exact feed composition, the exact solvent composition, the desired recovery and degree of purity of the cycloalkane product, and the like, and can be determined by those having ordinary skills in the art.

The invention can be better understood by reference to FIG. 1 and the following description of a preferred embodiment of the invention. The feed mixture comprising naphthenic and paraffinic hydrocarbons is introduced through conduit 10 to a fractionation zone such as multi-stage distillation column 12. The temperature of the feed mixture flowing through conduit 10 can be adjusted as needed by controlling heat exchanger 14 so as to add heat to or remove heat from the feed mixture. Solvent from solvent storage 6 is introduced to distillation column 12 through conduit 8, and an overhead stream enriched in paraffinic hydrocarbons (alkanes) is withdrawn from an upper portion of distillation column 12 through conduit 16. This overhead stream can be completely passed to storage or to other processing units or, as is often the case, the overhead stream can be partially or totally condensed, with a portion thereof being returned to the fractionation zone as reflux. The overhead stream passing through conduit 16 is condensed in condenser 22 to yield a condensed overhead stream. A portion of the condensed overhead stream can be returned to distillation column 12 as reflux through conduit 18, while the remainder of the condensed overhead stream is yielded as product or passed to other processing units through conduit 20.

A bottoms stream is withdrawn from a lower portion of the fractionation zone represented by distillation column 12 through conduit 24. A portion of the fluids withdrawn from the bottom of distillation column 12 may be heated and returned to distillation column 12. For example, a portion of the bottom products stream can be withdrawn through conduit 25, heated in reboiler 26 and then passed back to a lower portion of distillation column 12 through conduit 27.

Operating conditions in heat exchanger 14, condenser 22 and reboiler 26 can be controlled and interfaced with solvent flow through conduit 8, feed mixture flow through conduit 10, reflux flow through conduit 18 and bottom stream flow through conduit 24 such that the feed mixture introduced into distillation column 12 will be fractionated to yield an overhead stream which is enriched in paraffinic hydrocarbons and a bottoms stream predominantly comprising the naphthenic hydrocarbons and the solvent.

The bottoms stream passing through conduit 24 can be passed to storage, used in other processes or, preferably, passed to another fractionation zone, such as distillation column 29. Any adjustments to the temperature of the bottom stream passing through conduit 24 necessary for efficient fractionation in distillation column 29 can be made by appropriately adjusting heat exchanger 28. An overhead stream predominantly comprising naphthenic hydrocarbons is withdrawn from an upper portion of distillation column 29 through conduit 30. This overhead stream can be at least partially condensed in condenser 32. A portion of the overhead stream withdrawn from condenser 32 can be returned through conduit 34 as reflux for distillation column 29, with the remainder of the overhead stream being withdrawn as product, i.e., napthenic compounds (preferably cyclopentane and/or cyclohexane) of high purity (preferably higher than 95%), through conduit 36.

A bottoms stream predominantly comprising the solvent is withdrawn from a lower portion of distillation column 29 through conduit 38. A portion of this bottoms stream is preferably routed back to solvent storage 6 and then recycled to distillation column 12, while another portion of the bottoms stream is heated in a reboiler (not shown) and returned to the lower portion of column 29. From time to time, impurities which may build up in the solvent can be removed from the system by removing a small purge stream through conduit 40. Solvent lost through the purge stream or through other processing losses may be made up by a makeup stream passing through conduit 42 and into solvent storage 6.

The following examples are presented to further illustrate the invention and are not to be considered unduly limiting the scope of this invention.

EXAMPLE

This example demonstrates the superiority as extractant of a mixture of N-($\beta$-mercaptoehtyl)-2-pyrrolidone (NMEP) and either cyclohexanol (CHOL) or N-methyl-pyrrolidone (NMP) versus each component alone.

To a hydrocarbon mixture of 50 weight percent cyclopentane and 50 weight percent 2,2-dimethylbutane (2,2-DMB) was added an extractive solvent (either NMEP or CHOL or NMP or mixtures) at various solvent:feed weight ratios. The total mixture (including the extractive solvent) was heated under reflux conditions for about 20-30 minutes in a distillation flask equipped with a reflux condenser. Then a small sample was withdrawn by means of a septum from the flask containing the liquid phase of the equilibrium system, and a sample of the condensed vapor was withdrawn by means of a septum located just below the reflux condenser. Both samples were analyzed, and the mole fractions of 2,2-DMB and cyclopentane in the liquid phase and in the condensed vapor phase were determined. The relative volatility R was calculated as follows:

$$R = \frac{Y1/Y2}{X1/X2} = \frac{Y1/X1}{Y2/X2}$$

wherein Y1 and Y2 are the mole fractions of 2,2-DMB and cyclopentane respectively, in the vapor phase, and X1 and X2 are the mole fractions of 2,2-DMB and cyclopentane, respectively, in the liquid phase. Test results are summarized in Table I.

TABLE I

| Run | Solvent: Feed Wt. Ratio | Added Solvent | Relative Volatility R |
|---|---|---|---|
| 1 | 3:1 | NMEP | 1.28 |
| 2 | 3:1 | Mixture A of NMEP + CHOL | 1.40 |
| 3 | 3:1 | Mixture B of NMEP + CHOL | 1.42 |
| 4 | 3:1 | Mixture C of NMEP + NMP | 1.32 |
| 5 | 5:1 | NMEP | 1.48 |
| 6 | 5:1 | CHOL | 1.32 |
| 7 | 5:1 | NMP | 1.37 |
| 8 | 5:1 | Mixture A of NMEP + CHOL | 1.64 |
| 9 | 5:1 | Mixture B of NMEP + CHOL | 1.57 |
| 10 | 5:1 | Mixture C of NMEP + NMP | 1.54 |
| 11 | 7:1 | NMEP | 1.71 |
| 12 | 7:1 | CHOL | 1.26 |
| 13 | 7:1 | NMP | 1.33 |
| 14 | 7:1 | Mixture A of NMEP + CHOL | 1.70 |
| 15 | 7:1 | Mixture B of NMEP + CHOL | 1.64 |
| 16 | 7:1 | Mixture C of NMEP + NMP | 1.74 |

Notes:
(1)Mixture A contained 9 parts by weight of NMEP and 1 part by weight of CHOL.
(2)Mixture B contained 4 parts by weight of NMEP and 1 part by weight of CHOL.
(3)Mixture C contained 9 parts by weight of NMEP and 1 part by weight of NMP.
(4)Two liquid phases were present during the equilibrium state of all runs, with the exception of runs 9, 14 and 15.

Test data in Table I clearly show that mixtures of N-(β-mercaptoethyl)-2-pyrrolidone with either cyclohexanol or N-methyl-2-pyrrolidone generally exhibited higher relative volatilities than N-(β-mercaptoethyl)-2-pyrrolidone alone or cyclohexanol alone or N-methyl-2-pyrrolidone alone, and thus are expected to be more effective as solvents (extractants) in the separation of a cycloalkane from a close-boiling isoalkane by extractive distillation than the single compounds. Additional data (not listed in Table I) for a solvent:feed ratio of 1:1 showed that the relative volatility was 1.12–1.14 for mixtures A, B and C versus a relative volatility of 1.08 for MMEP alone. Results similar to those listed in Table I were obtained in tests using Solvent Mixture A in the extractive distillation of a mixture of cyclohexane and 2,4-dimethylpentane.

Reasonable variations, modifications and adaptations for various usages and conditions can be made within the scope of the disclosure and the appended claims, without departing from the scope of this invention.

That which is claimed is:

1. In a process for separating at least one cycloalkane containing 5–10 carbon atoms per molecule from at least one close-boiling alkane by extractive distillation of a feed consisting essentially of said at least one cycloalkane and said at least one alkane,
the improvement comprising the use of a solvent consisting essentially of a mixture of (a) at least one N-mercaptoalkyl-2-pyrrolidone, wherein the mercaptoalkyl group contains 1–5 carbon atoms, and (b1) at least one N-alkyl-2-pyrrolidone, wherein the alkyl group contains 1–3 carbon atoms;
wherein said extractive distillation process produces (i) an overhead distillate product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkane than said feed; and wherein said at least one cycloalkane is separated from said solvent and recovered from said bottoms product.

2. A process in accordance with claim 1, wherein component (a) of said solvent is N-(β-mercaptoethyl)-2-pyrrolidone.

3. A process in accordance with claim 1, wherein component (b1) of said solvent is N-methyl-2-pyrrolidone.

4. A process in accordance with claim 1 wherein component (a) of said solvent is N-(β-mercaptoethyl)-2-pyrrolidone and component (b1) of said solvent is N-methyl-2-pyrrolidone.

5. A process in accordance with claim 1, wherein said at least one cycloalkane is selected from the group consisting of cyclopentane, cyclohexane and mixtures thereof.

6. A process in accordance with claim 1, wherein said at least one cycloalkane is selected from the groups consisting of cyclopentane, cyclohexane and mixtures thereof, and said at least one alkane is at least one close-boiling isoalkane.

7. A process in accordance with claim 1, wherein the weight ratio of component (a) to component (b1) in said solvent is in the range of from about 0.1:1 to about 20:1.

8. A process in accordance with claim 7, wherein component (a) of said solvent is N-(β-mercaptoethyl)-2-pyrrolidone and component (b1) of said solvent is N-methyl-pyrrolidone.

9. A process in accordance with claim 1, wherein the weight ratio of said solvent to said feed is in the range of from about 0.5:1 to about 50:1.

10. A process in accordance with claim 1, wherein said feed boils at a temperature in the range of from about 80° F. to about 350° F., at a pressure of about 1 atm.

11. A process in accordance with claim 1, wherein the boiling point of said at least one cycloalkane and the boiling point of said at least one alkane differ about 0.2° F. to about 10° F. at a pressure of about 1 atm.

12. In a process for separating at least one cycloalkane containing 5–10 atoms per molecule from at least one close-boiling alkane by extractive distillation of a feed consisting essentially of said at least one cycloalkane and said at least one alkane,
the improvement comprising the use of a solvent consisting essentially of a mixture of (a) at least one N-mercaptoalkyl-2-pyrrolidone, wherein the mercaptoalkyl group contains 1–5 carbon atoms, and (b2) at least one saturated alcohol selected from the group consisting of alkanols and cycloalkanols containing 5–9 carbon atoms and 1 OH group per molecule;

wherein said extractive distillation process produces (i) an overhead distillate product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkane than said feed; and wherein said at least one cycloalkane is separated from said solvent and recovered from said bottoms product.

13. A process in accordance with claim 12, wherein component (a) of said solvent is N-(β-mercaptoethyl)-2-pyrrolidone.

14. A process in accordance with claim 12, wherein component (b2) of said solvent is cyclohexanol.

15. A process in accordance with claim 12, wherein component (a) of said solvent is N-(β-mercaptoethyl)-2-pyrrolidone, and component (b2) of said solvent is cyclohexanol.

16. A process in accordance with claim 12, wherein said at least one cycloalkane in said feed is selected from the group consisting of cyclopentane, cyclohexane and mixtures thereof.

17. A process in accordance with claim 12, wherein said at least one cycloalkane in said feed is selected from the group consisting of cyclopentane, cyclohexane and mixtures thereof, and said at least one alkane in said feed is at least one close-boiling isoalkane.

18. A process in accordance with claim 12, wherein the weight ratio of component (a) to component (b2) in said solvent is in the range of from about 0.1:1 to about 20:1.

19. A process in accordance with claim 18, wherein said component (a) is N-(β-mercaptoethyl)-2-pyrrolidone, and said component (b2) is cyclohexanol.

20. A process in accordance with claim 12, wherein the weight ratio of said solvent to said feed is in the range of from about 0.5:1 to about 50:1.

21. A process in accordance with claim 12, wherein said feed boils at a temperature in the range of from about 80° F. to about 350° F., at a pressure of about 1 atm.

22. A process in accordance with claim 12, wherein the boiling point of said at least one cycloalkane and the boiling point of said at least one alkane differ about 0.2° to about 10° F., at a pressure of about 1 atm.

23. In a process for separating at least one cycloalkane containing 5-10 carbon atoms per molecule from at least one close-boiling alkane by extractive distillation of a feed consisting essentially of said at least one cycloalkane and said at least one alkane, the improvement comprising the use of a solvent consisting essentially of a mixture of
(a) at least one N-mercaptoalkyl-2-pyrrolidone, wherein the mercaptoalkyl group contains 1-5 carbon atoms,
(b1) at least one N-alkyl-2-pyrrolidone, wherein the alkyl group contains 1-3 carbon atoms, and
(b2) at least one saturated alcohol selected from the group consisting of alkanols and cycloalkanols containing 5-9 carbon atoms and 1 OH group per molecule;

wherein said extractive distillation process produces (i) an overhead distillate product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkanes than said feed; and wherein said at least one cycloalkane is separated from said solvent and recovered from said bottoms product.

24. A process in accordance with claim 23, wherein component (a) of said solvent is N-(β-mercaptoethyl)-2-pyrrolidone, component (b1) of said solvent is N-methyl-2-pyrrolidone, and component (b2) of said solvent is cyclohexanol.

25. A process in accordance with claim 23, wherein said at least one cycloalkane is selected from the group consisting of cyclopentane, cyclohexane and mixtures thereof.

26. A process in accordance with claim 23, wherein the weight ratio of component (a) to the sum of components (b1) and (b2) in said solvent is in the range of from about 0.1:1 to about 20:1.

27. A process in accordance with claim 23, wherein the weight ratio of said solvent to said feed is in the range of from about 0.5:1 to about 5:1.

* * * * *